United States Patent
Lazzari et al.

(10) Patent No.: US 12,097,005 B2
(45) Date of Patent: Sep. 24, 2024

(54) TRANSMISSION SYSTEM OF A SURGICAL INSTRUMENT FOR ROBOTIC SURGERY

(71) Applicant: MEDICAL MICROINSTRUMENTS, INC., Wilmington, DE (US)

(72) Inventors: Giorgio Lazzari, Pisa (IT); Massimiliano Simi, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 0 days.

(21) Appl. No.: 18/694,624

(22) PCT Filed: Sep. 22, 2022

(86) PCT No.: PCT/IB2022/058962
§ 371 (c)(1),
(2) Date: Mar. 22, 2024

(87) PCT Pub. No.: WO2023/047325
PCT Pub. Date: Mar. 30, 2023

(65) Prior Publication Data
US 2024/0261050 A1    Aug. 8, 2024

(30) Foreign Application Priority Data

Sep. 24, 2021   (IT) .................. 102021000024554

(51) Int. Cl.
*A61B 34/00*     (2016.01)
*A61B 34/30*     (2016.01)
(52) U.S. Cl.
CPC .............. *A61B 34/71* (2016.02); *A61B 34/30* (2016.02)
(58) Field of Classification Search
CPC .. F16D 1/10; F16J 15/50; A61B 17/00; A61B 2017/00398; A61B 2017/0046;
(Continued)

(56) References Cited

U.S. PATENT DOCUMENTS

| 8,142,447 B2 | 3/2012 | Cooper |
| 10,582,975 B2 | 3/2020 | Simi |

(Continued)

FOREIGN PATENT DOCUMENTS

| EP | 3586780 A1 | 1/2020 |
| WO | 2017064301 A1 | 4/2017 |

(Continued)

OTHER PUBLICATIONS

International Search Report and Written Opinion received for PCT Serial No. PCT/IB2022/058962 on Dec. 15, 2022, 10 pgs.

(Continued)

*Primary Examiner* — Scott Luan
(74) *Attorney, Agent, or Firm* — Merchant & Gould P.C.

(57) ABSTRACT

A surgical instrument for robotic surgery includes a tendon-actuated articulating end, an actuating tendon, and a backend portion having an elongated transmission body movable along a longitudinal direction coinciding with or parallel to a longitudinal extension axis of the elongated body. A first resting wall forms a first resting part for a first transversal side of the elongated body. A second resting part is for a second transversal side, opposite to the first transversal side, of the elongated body. The actuating tendon is operatively connected to the elongated body and is operatively connected to a return element. The elongated body includes on the first side thereof a first lateral surface which slidably rests against the first resting wall; the elongated body includes on the second side a second lateral surface which slidably rests against the second resting part.

14 Claims, 12 Drawing Sheets

(58) Field of Classification Search
CPC ... A61B 2090/064; A61B 34/30; A61B 34/76; A61B 46/10
See application file for complete search history.

(56) References Cited

U.S. PATENT DOCUMENTS

| | | |
|---|---|---|
| 10,864,051 B2 | 12/2020 | Simi |
| 2015/0173730 A1 | 6/2015 | Lohmeier |
| 2019/0159853 A1 | 5/2019 | Haraguchi |
| 2020/0170726 A1 | 6/2020 | Simi |
| 2020/0170727 A1 | 6/2020 | Simi |
| 2021/0059776 A1 | 3/2021 | Simi |
| 2021/0137618 A1 | 5/2021 | Simi |

FOREIGN PATENT DOCUMENTS

| | | |
|---|---|---|
| WO | 2018189721 A1 | 10/2018 |
| WO | 2018189722 A1 | 10/2018 |
| WO | 2018189729 A1 | 10/2018 |
| WO | 2019220407 A1 | 11/2019 |
| WO | 2019220408 A1 | 11/2019 |
| WO | 2019220409 A1 | 11/2019 |

OTHER PUBLICATIONS

International Preliminary Report on Patentability received for PCT Serial No. PCT/IB2022/058962 on Dec. 22, 2023, 7 pgs.

TRANSMISSION SYSTEM OF A SURGICAL INSTRUMENT FOR ROBOTIC SURGERY

CROSS-REFERENCE TO RELATED APPLICATIONS

This application is the National Phase of International Application No. PCT/IB2022/058962, filed on Sep. 22, 2022, which claims the priority to Italian Patent Application No. 102021000024554, filed on Sep. 24, 2021, the entire contents of which are incorporated into this application by reference.

FIELD OF THE INVENTION

The present invention relates to a surgical instrument. Furthermore, the present invention relates to a robotic surgery system comprising said surgical instrument.

BACKGROUND ART

Robotic surgery apparatuses are generally known in the art and typically comprise a central robotic tower (or cart) and one or more robotic arms extending from the central robotic tower. Each arm comprises a motorized positioning system (or manipulator) for moving a surgical instrument distally attachable thereto, in order to perform surgical procedures on a patient. The patient typically lies on an operating bed located in the operating room, in which sterility is ensured to avoid bacterial contamination due to non-sterile parts of the robotic apparatus.

U.S. Ser. No. 10/864,051, WO-2017-064301, WO-2019-220407, WO-2019-220408, WO-2019-220409 and US-2021-059776 to the same Applicant disclose teleoperated robotic surgery systems having one or more surgical instruments controlled by one or more master interfaces.

Generally, known surgical instruments for teleoperated robotic surgery comprise a proximal interface portion (or backend portion, according to a terminology commonly adopted in the field) having an interface intended to be operated by a robotic manipulator, an elongated element such as a rod or a shaft, an articulated device (e.g., a robotic wrist), and an operating terminal end (e.g., needle-driver, scissors).

In the known surgical instruments having an articulated cuff, it consists of a plurality of links moved by a plurality of tendons (or actuating cables). One or more terminal links can have a free end forming the aforementioned operating end, and are for example adapted to operate directly on a patient's anatomy and/to handle a needle as well as a suture thread for performing anastomoses or other surgical therapies.

Unlike the known surgical instruments comprising an articulated cuff, surgical instruments having an articulated device of the "snake" type are also known, i.e., comprising a plurality of stacked vertebrae which are movable with respect to each other by means of a plurality of actuating cables or tendons.

The proximal interface (or backend) portion of the surgical instrument typically comprises movable interface bodies operatively connected with the actuating tendons, for controlling the end-effector of the surgical instrument itself, and adapted to engage with a counter-portion of the actuating interface of the robotic manipulator, as for example shown by U.S. Pat. No. 8,142,447.

In fact, in the field of robotic surgery, the surgical instrument is a component intended to operate in a sterile environment and typically a sterile barrier is interposed between the backend portion of the instrument and the counter-portion of the actuation interface, so that the robotic manipulator is in the non-sterile region of the operating set-up. Therefore, the motors are normally placed in the manipulator, i.e., on the non-sterile side, and the surgical instrument lacks motors.

The known transmission elements at the proximal backend interface of the surgical instrument can be made in the form of winches or spools adapted to unwind and wind a portion of the tendon associated therewith, and correspondingly the motorized actuators of the robotic manipulator can be rotary actuators. The engagement between rotary motorized actuators and corresponding spools of the surgical instrument through the sterile barrier can be facilitated by the inclusion of rigid inserts such as vanes on the sterile barrier.

Otherwise, robotic systems for surgery are also known which use linear actuators, for example motorized pistons, adapted to impart to the respective transmission elements a controlled linear displacement under the control of appropriate electronic control means, as for example shown in WO-2018-189729, on behalf of the same Applicant, and in US-2015-0173730.

Therefore, in the backend portion of the surgical instrument, a plurality of transmission pistons is included, adapted to advance and retract along a straight path, which expose a contact surface thereof, proximally, in relief with respect to the proximal interface surface of the instrument, so that they can be stressed by the motorized actuators. Distally, such transmission pistons are operatively connected or connectable to respective actuating tendons. A spring affects the transmission pistons inside the body of the backend portion of the instrument to maintain a minimum state of tension on the tendons operatively connected thereto.

U.S. Ser. No. 10/582,975, EP-3586780, WO-2017-064303, WO-2017-064306, WO-2018-189721, WO-2018-189722, US-2020-0170727 and US-2020-0170726 on behalf of the same Applicant disclose various embodiments of surgical instruments for robotic surgery and microsurgery designed to be subject to an extreme miniaturization of the articulated cuff and therefore of the operating end or end-effector.

As the size of the articulated cuff actuated by means of tendons decreases, clearly, each longitudinal shortening or lengthening of the length of a tendon activates a corresponding angular movement of the cuff which gradually increases in magnitude. This requires that boosted tolerances be respected in the backend portion of the surgical instrument.

In the case of using linear transmission pistons included in the backend portion, it is common practice to provide each elongated body with a pair of recirculating sliding ball bushings which are fixed to the body of the backend portion of the surgical instrument. Typically, the two bushings of the pair are arranged at opposite ends of the elongated transmission body.

However, the choice to use such sliding bushings is by no means without drawbacks.

In fact, recirculating ball bushings are expensive components, and require boosted coupling tolerances with the elongated body, as well as boosted longitudinal alignment tolerances, and also careful maintenance to avoid frequent malfunctions. For example, the elongated body could suddenly interlock in the bushing and transmit a tearing motion.

In addition, having to include two bushings imposes a relatively large dimension of the backend portion body, as well as a certain minimum length of the transmission pistons, because the two bushings must be mounted sufficiently spaced from each other to acceptably guide the elongated body, and in fact reduce the extent of the stroke of the elongated body, necessarily forming a central length of the elongated body which does not work.

Eliminating one of the two bushings of the pair would not solve the problem, because although on the one hand it would allow gains in terms of stroke of the elongated body with the same overall dimensions, i.e., length thereof, on the other hand it would impose even more frequent static and dynamic frictions due, for example, to impingements of the elongated body caused by minimum angular oscillations of the elongated body in the single residual bushing and/or minimum flexural deformations of the elongated body, causing a tearing transmission with the result that some of the tendons could suddenly be loose and not taut, and could therefore slip off, i.e., decouple, from the return elements where included, and this is certainly undesirable in the field of robotic surgery.

The need is therefore felt to provide a surgical instrument for robotic surgery suitable for an extreme miniaturization.

Furthermore, the need is felt to make a miniaturized surgical instrument provided with a transmission of the action imparted by the motorized actuators of the robotic system for reliable, repeatable, and safe surgery, without imposing increased dimensions of the components thereof.

Furthermore, in a miniaturized surgical instrument for robotic surgery having transmission pistons of the action imparted by the motorized actuators of the robotic system, the need is felt to increase the useful stroke of the pistons with equal longitudinal dimensions of the elongated body and of the backend portion of the surgical instrument, as well as the need is felt to reduce the longitudinal dimensions with an equal useful stroke of the elongated body.

SOLUTION

It is an object of the present invention to obviate the drawbacks complained of with reference to the background art.

By virtue of the proposed solutions, it is possible to avoid including a pair of sliding linear bushings fitted on each elongated transmission body.

By virtue of the proposed solutions, a transmission action is achieved which is more reliable and repeatable with respect to known solutions of surgical instruments actuated by actuating tendons.

BRIEF DESCRIPTION OF THE DRAWINGS

Further features and advantages of the invention will become apparent from the following description of preferred examples of embodiments, given by way of non-limiting example, with reference to the accompanying drawings which are briefly described below. It should be noted that references to "an" embodiment in this disclosure do not necessarily refer to the same embodiment, and are to be understood as at least one. Furthermore, for reasons of conciseness and reduction of the total number of figures, a certain figure can be used to illustrate the features of more than one embodiment, and not all elements of the figure may be necessary for a certain embodiment.

DETAILED DESCRIPTION OF SOME EMBODIMENTS

Figure 1:
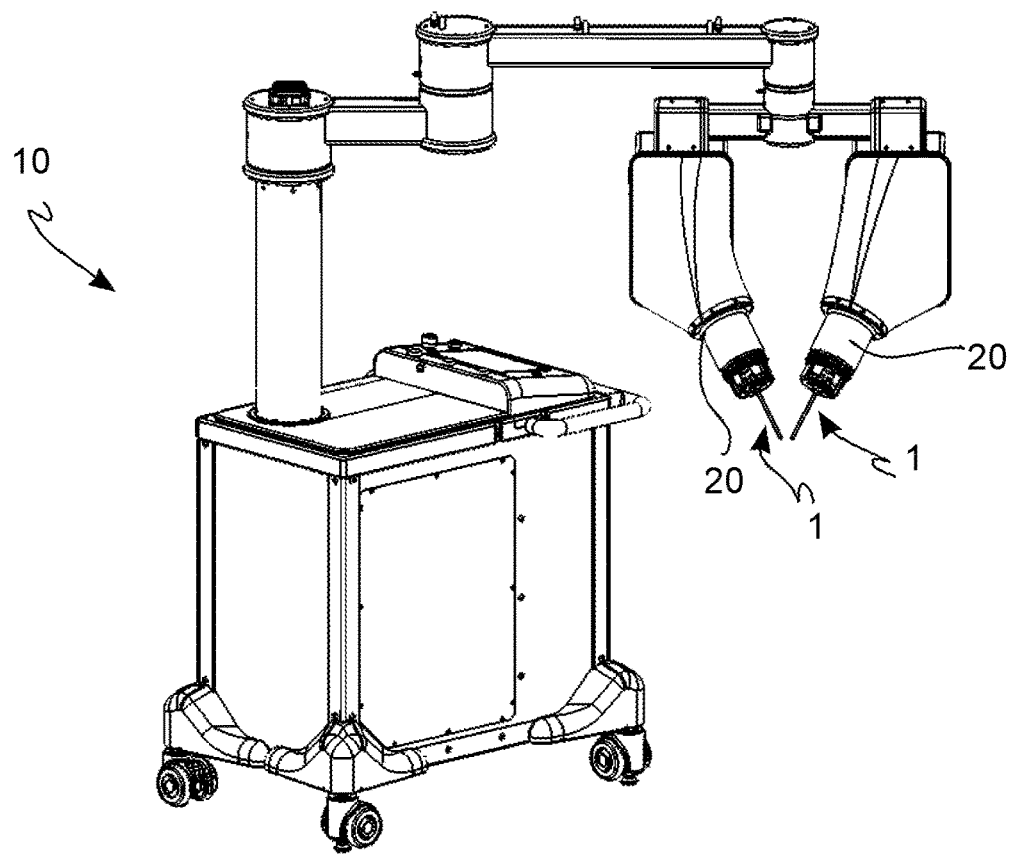
FIG. 1 is an axonometric view showing a robotic surgery system, according to an embodiment.
Figure 2:
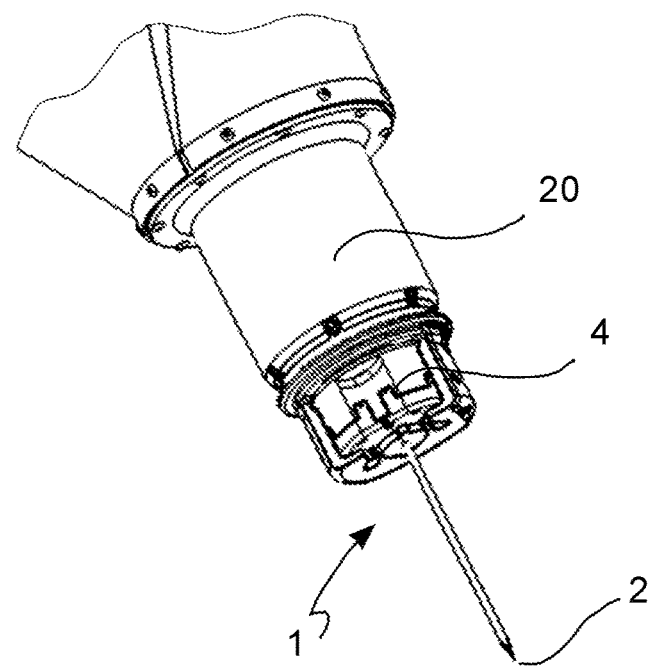
FIG. 2 is an axonometric view showing a surgical instrument associated with a robotic manipulator of a robotic surgery system, according to an embodiment.
Figure 3:
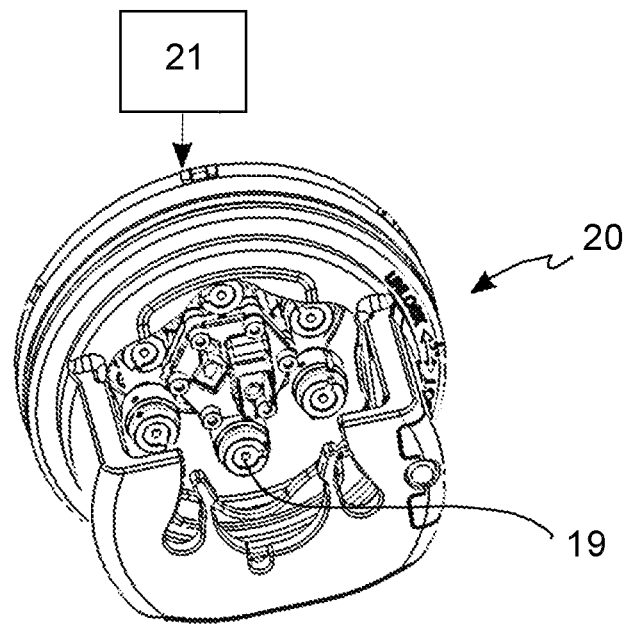
FIG. 3 is an axonometric view showing a robotic manipulator, according to an embodiment, in which a control device is diagrammatically shown.

Reference throughout this description to "an embodiment" is meant to indicate that a particular feature, structure or function described in relation to the embodiment is included in at least one embodiment of the present invention. Therefore, the formulation "in an embodiment" in various parts of this description do not necessarily all refer to the same embodiment. Furthermore, particular features, structures or functions such as those shown in different drawings can be combined in any suitable manner in one or more embodiments.

In accordance with a general embodiment, a surgical instrument 1 for robotic surgery is provided comprising a tendon-actuated articulating end 2, and at least one actuating tendon 3. The actuating tendon 3 can be a polymeric tendon formed by braided polymeric fibers. The articulating end 2 can be an articulated cuff type end comprising a rotational joint of pitch and/or yaw, or it can be a "snake" type end comprising a plurality of vertebrae.

The surgical instrument 1 further comprises a transmission interface portion 4 or backend portion 4. Preferably the backend portion 4 is arranged proximally with respect to the articulating end 2. Between the backend portion 4 and the articulating end 2, a stick 17 or rod 17 or shaft 17 can be included, made rigid or flexible.

The backend portion 4 of the surgical instrument 1 comprises at least one elongated transmission body 5 (hereinafter also only "elongated body") movable along a longitudinal direction X-X which is coinciding with or parallel to a longitudinal extension axis of said at least one elongated body 5. For example, said at least one elongated transmission body 5 comprises a transmission piston and/or a transmission rod.

According to a preferred embodiment, said at least one elongated transmission body 5 comprises an interface surface 18 adapted to receive a pushing action exerted by a motorized actuator 19 of a robotic manipulator 20 of a robotic surgery system 10. A sterile barrier (not shown) can be interposed between the motorized actuator 19 of the robotic manipulator 20 and the interface surface 18 of the elongated transmission body 5, so that the pushing action exerted by the motorized actuator 19 is transmitted to the elongated body 5 through the sterile barrier body.

An electronic control device 21 can be operatively connected to the robotic manipulator 20 so that the at least one motorized actuator 19 imparts the pushing action on the elongated body 5 under the control of the control device 21.

The at least one actuating tendon 3 is operatively connected to said elongated transmission body 5. Thereby, the pushing action exerted by the motorized actuator 19 is transmitted to the at least one actuating tendon 3 by means of the elongated body 5. According to a preferred embodiment, the at least one actuating tendon 3 is integral with the elongated body 5. For example, a head 31 of the actuating tendon 3 is terminated secured to the elongated transmission body 5.

Preferably, the pushing action imparted by the motorized actuator 19 on the respective elongated body 5 is transmitted substantially equal to the actuating tendon 3 in the form of a traction action to actuate at least one degree of freedom (e.g., pitch and/or yaw and/or grip) of the articulating end 2 of the surgical instrument 1.

The backend portion 4 of the surgical instrument 1 further comprises at least one resting wall 6 forming a first resting part for a first transversal side 51 of the at least one elongated body 5. Therefore, the at least one elongated body 5 comprises on the first side 51 thereof a first lateral surface 11 which slidably rests against said at least one resting wall 6.

The backend portion 4 of the surgical instrument 1 further comprises at least a second resting part 7 for a second transversal side 52, opposite to said first transversal side 51, of the at least one elongated body 5. Therefore, the at least one elongated body 5 comprises on the second side 52 a second lateral surface 12 which slidably rests against said second resting part 7.

According to an embodiment, said second resting part 7 comprises a low friction support surface, for example made of or coated with low friction polymeric material such as PTFE and/or UHMWPE.

The elongated transmission body 5 can be made of polished and/or ground metal, or can be made of low friction polymeric material such as PTFE.

When in operating conditions, the pushing action P5 imparted by the motorized actuator 19 determines the sliding of the elongated body 5 along the longitudinal axis X-X with respect to said first resting surface 6 and to said second resting part 7 of the backend portion 4.

Preferably, the backend portion 4 of the surgical instrument 1 further comprises at least one return element 8 for returning the at least one actuating tendon 3, in which the at least one actuating tendon 3 is operatively connected to said at least one return element 8.

By virtue of the inclusion of said at least one return element 8, it is possible to locate the traction action T3 of the actuating tendon 3 at a certain distance D3 from the longitudinal axis X-X of the elongated transmission body 5. In this manner, when in operating conditions, a torque is formed which tends to bring the second side 52 of the elongated body 5 closer to the second resting part 7 and at the same time tends to bring the first side 51 of the elongated body closer to the first resting part 6.

The balance of the transversal forces is given by the transversal reactions Y6, Y7 to the sliding rests of the elongated body 5 on the first and second resting surfaces 6, 7.

In accordance with a preferred embodiment, said resting wall 6 forming a first resting part for said first side 51 of the at least one elongated body 5 comprises a curved and convex resting surface. Preferably, the first lateral surface 11 of the first side 51 of the elongated body is convex, i.e., it forms a protrusion, for example a toroidal protrusion surrounding the opening in which the body slides. For example, the first convex lateral surface 11 can be a broken surface, for example given by the union of two cones having a base at the sliding resting point with the elongated body 5.

Even more preferably, the first lateral surface 11 of the first side 51 of the elongated body is curved and convex, for example substantially cylindrical, for example cylindrical around the longitudinal extension axis X-X of the elongated body 5, so as to form a spherical rest (or spherical hinge). In other words, the curved and convex lateral surface 11 of the elongated body 5 and the resting surface of the curved and convex resting wall 6 form a spherical joint or spherical hinge while allowing the longitudinal sliding of the elongated body 5. In this manner, risks of impingement of the elongated transmission body 5 when in operating conditions are avoided, or at least minimized. Therefore, the elongated body 5 can be made compact, reducing the longitudinal dimensions of the backend portion 4.

In accordance with an embodiment, at least the proximal section of the elongated body 5 is substantially cylindrical, for example has cylindrical geometry around the longitudinal extension axis X-X of the elongated body 5.

In accordance with an embodiment, at least the proximal portion of the elongated body 5 is substantially cylindrical. The distal portion can comprise for example an enlarged portion which does not have a cylindrical geometry.

In accordance with an embodiment, the elongated body 5 is a cylindrical body having a cylindrical outer surface around the longitudinal extension axis X-X of the elongated transmission body 5, in which said cylindrical outer surface comprises said curved and convex resting surface of the resting wall 6.

In accordance with a preferred embodiment, said backend 4 further comprising at least one pivotable organ 13, in which said second resting part 7 belongs to said pivotable organ 13. For example, said pivotable organ 13 is a wheel, and/or an idle pulley, and/or a rolling bearing. By virtue of the inclusion of said second resting part 7 for the second side 52 of the elongated body made on a pivotable organ 13, the sliding rest determines the rolling of the pivotable organ 13 on the lateral surface 12 of the elongated body 5, when in operating conditions.

The axis of rotation R-R of the pivotable organ 13 is preferably fixed with respect to the backend portion 4. In other words, the axis of rotation R-R of the pivotable organ 13 is preferably fixed with respect to said first resting surface 6 forming the first sliding resting part.

The axis of rotation R-R of the pivotable organ 13 is preferably transversal with respect to the longitudinal direction X-X of the elongated body 5.

According to a preferred embodiment, said pivotable organ 13 further comprises said return element 8. In other words, the proximal interface portion 4 comprises a pivotable organ 13 for the actuating tendon 3 and which forms a rolling sliding rest for said elongated body 5. Thereby, said pivotable organ 13 assumes the dual function of return of the actuating tendon 3 and of sliding rolling rest for said elongated transmission body 5. The rotation of the pivotable organ 13 can be determined by the sliding rolling rest alone, or also by the rotating drag exerted by the actuating tendon 3 mounted to the pivotable organ 13.

The sliding friction of the at least one actuating tendon 3 on the return element 8 can be so low that the actuating tendon 3 slides on the return element 8 without dragging it in rotation.

In accordance with an embodiment, said at least one elongated body 5 comprises a longitudinal rail 9 which receives at least one portion of said pivotable organ 13.

In accordance with an embodiment, between the second side 52 of the at least one elongated body 5 and the at least one pivotable organ 13, a recess 15 is included which receives the actuating tendon 3, avoiding interposing with contact, and thus crushing, the actuating tendon 3 between the pivotable organ 13 and the elongated body 5.

In accordance with a preferred embodiment, said backend 4 further comprises at least one elastic element 14 operatively connected to said at least one elongated body 5, which biases said at least one actuating tendon 3. Preferably, the elastic element 14 tends to move the elongated transmission body 5 away from the respective motorized actuator 19 along the longitudinal direction X-X.

In accordance with an embodiment, said elongated body 5 comprises a first longitudinal section 53 comprising said interface surface 18, and a second longitudinal section 54 which is longitudinally opposite with respect to said first longitudinal section 53. For example, said first longitudinal section 53 is arranged proximal with respect to said second longitudinal section 54, which will therefore be placed distal with respect to the first longitudinal section 53. In accordance with a preferred embodiment, said first resting surface 6 makes the rest on said first longitudinal section 53 and while the second opposite resting part 7 makes the rest on said second longitudinal section 54 of the elongated transmission body 5.

In accordance with an embodiment, the second longitudinal section 54 of said elongated body 5 comprises a wall 23 adapted to form a further resting part for said first side 51 of the elongated body 5, to limit the transversal distancing of the elongated body with respect to the second resting part 7 placed on the second side 52, and preferably placed on a transversal relief of the elongated body 5. In other words, the wall 23 is facing away with respect to the second lateral surface 12 and is placed on the second longitudinal section 54 of the elongated body 5.

In accordance with an embodiment, the second longitudinal section 54 of said elongated body 5 comprises a transversally enlarged portion 22, for example made in a separate piece and then fixed to the elongated body 5 such as a tensioner 22, which comprises said second lateral surface 12 in sliding rest on said second resting part 7 of the backend portion 4. Preferably, the enlarged portion 22 comprises at least one longitudinally facing abutment wall 24 forming an abutment for said elastic element 14. Preferably, the elastic element 14 works between said abutment wall 24 of the enlarged portion 22 of the elongated body 5 and an opposite second resting part 25 of the backend portion 4.

The enlarged portion 22 can comprise said rail 9 and/or can comprise the end of the head 31 of the actuating tendon 3.

In accordance with an embodiment, said first resting wall 6 forming the first resting part for the first transversal side 51 of the elongated body 5 belongs to a hole edge delimiting a through hole in the body of the backend portion 4. Said hole edge can have a substantially toroidal geometry, making a spherical rest (or spherical hinge). Said hole edge can comprise a further wall 26 facing the second transversal side 52 of the elongated body 5, and said further wall 26 can also form a spherical rest.

Figure 5:
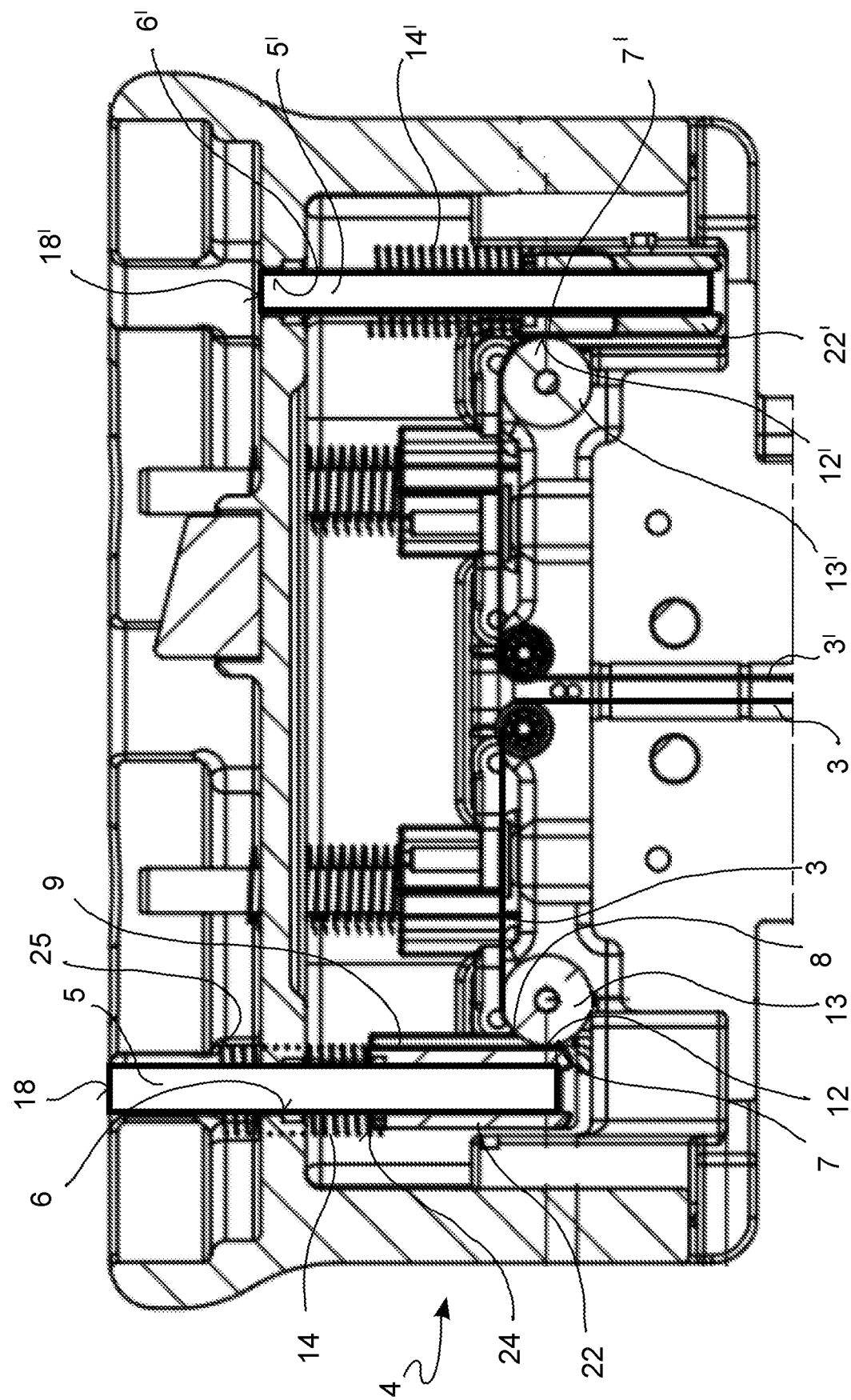
FIG. 5 is a sectional view showing a backend portion of a surgical instrument, according to an embodiment.
Figure 6:
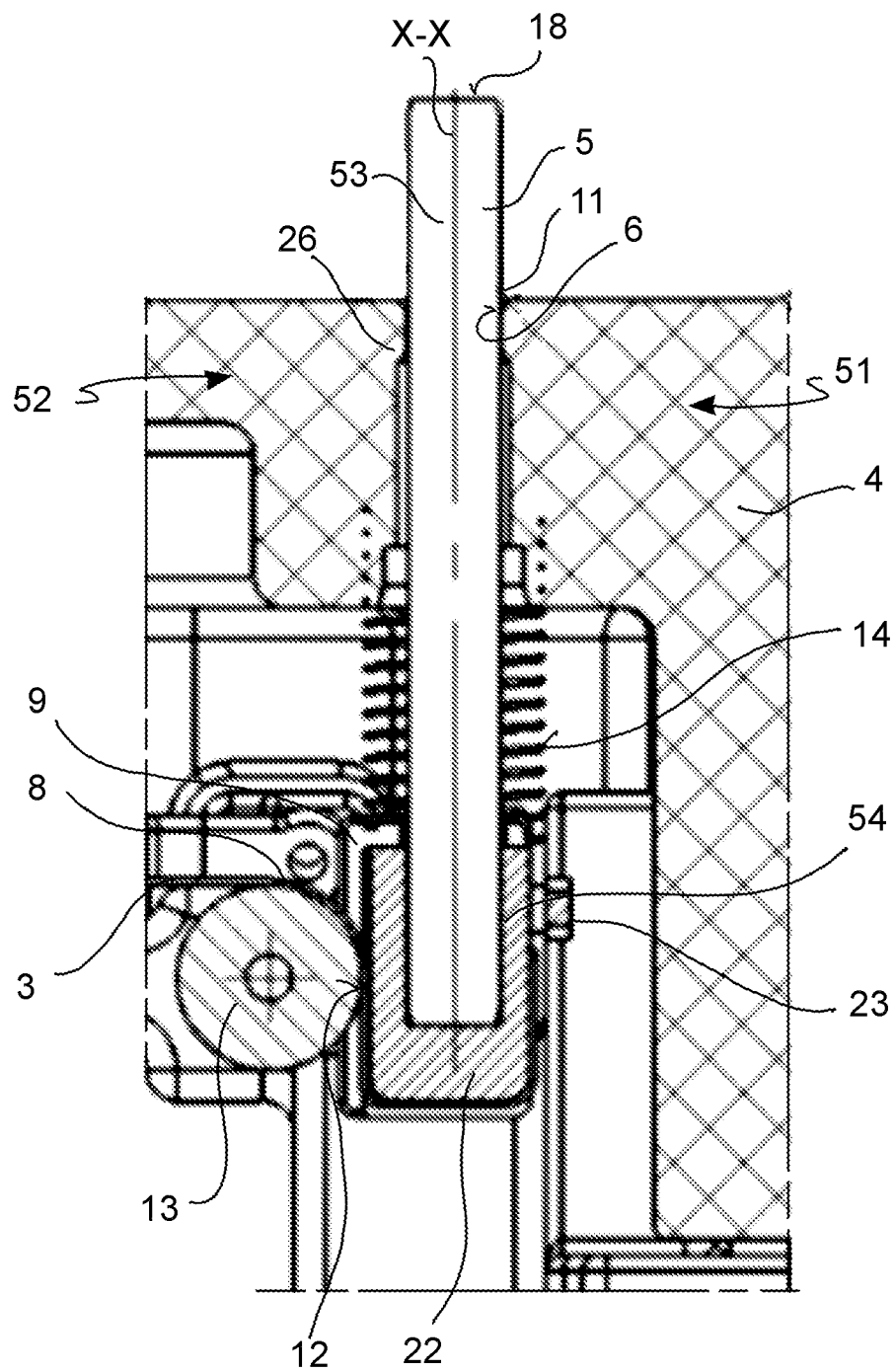
FIG. 6 is a sectional view showing a backend portion of a surgical instrument, according to an embodiment.
Figure 7:
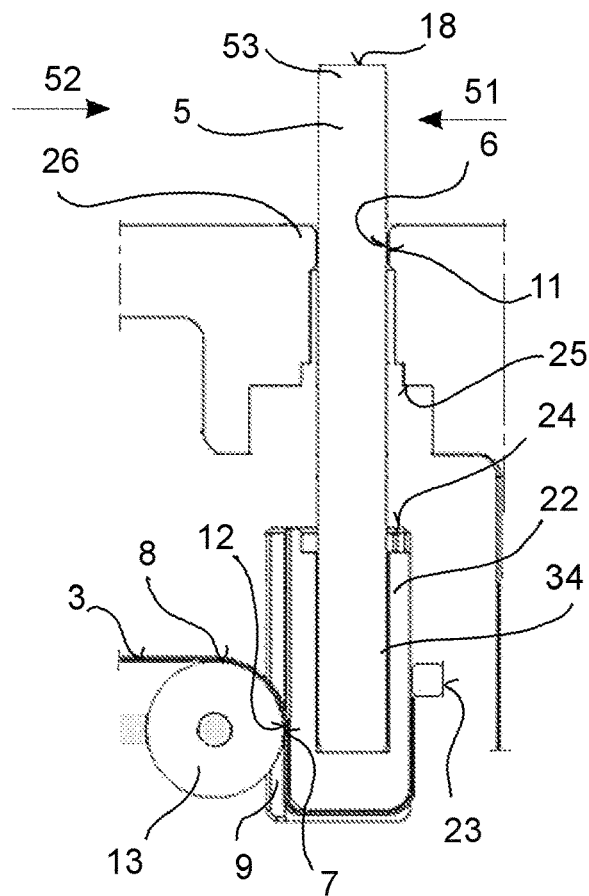
FIG. 7 is a sectional view showing a backend portion of a surgical instrument, according to an embodiment.

In accordance with a preferred embodiment, as shown for example in FIG. 5, a degree of freedom of the articulating end 2 of the surgical instrument 1 is operatively connected to two antagonist actuating tendons 3, 3' comprising said at least one actuating tendon 3 and a second antagonist actuating tendon 3'. In such a case, both antagonist actuating tendons 3, 3' are associated with respective elongated transmission bodies 5, 5', each of which being operatively associated with at least one resting wall 6, 6' forming a first resting part for a first transversal side of each elongated body 5, 5' and at least a second resting part 7, 7' on which rests a lateral surface 12, 12' of the elongated transmission body 5, and at least one return element 8, 8' for each actuating tendon 3, 3'. Therefore, similar to what is described above, each elongated transmission body 5, 5' can be operatively connected to a respective return element 8, 8' and/or to a respective pivotable organ 13, 13'. Furthermore, similar to what is described above, each elongated transmission body 5, 5' can be operatively connected to a respective elastic element 14, 14'. Furthermore, similar to what is described above, each elongated transmission body 5, 5' can comprise an interface surface 18, 18' adapted to receive a pushing action from a respective motorized actuator. Furthermore, similar to what is described above, each elongated transmission body 5, 5' can comprise an enlarged portion 22'.

Figure 4:
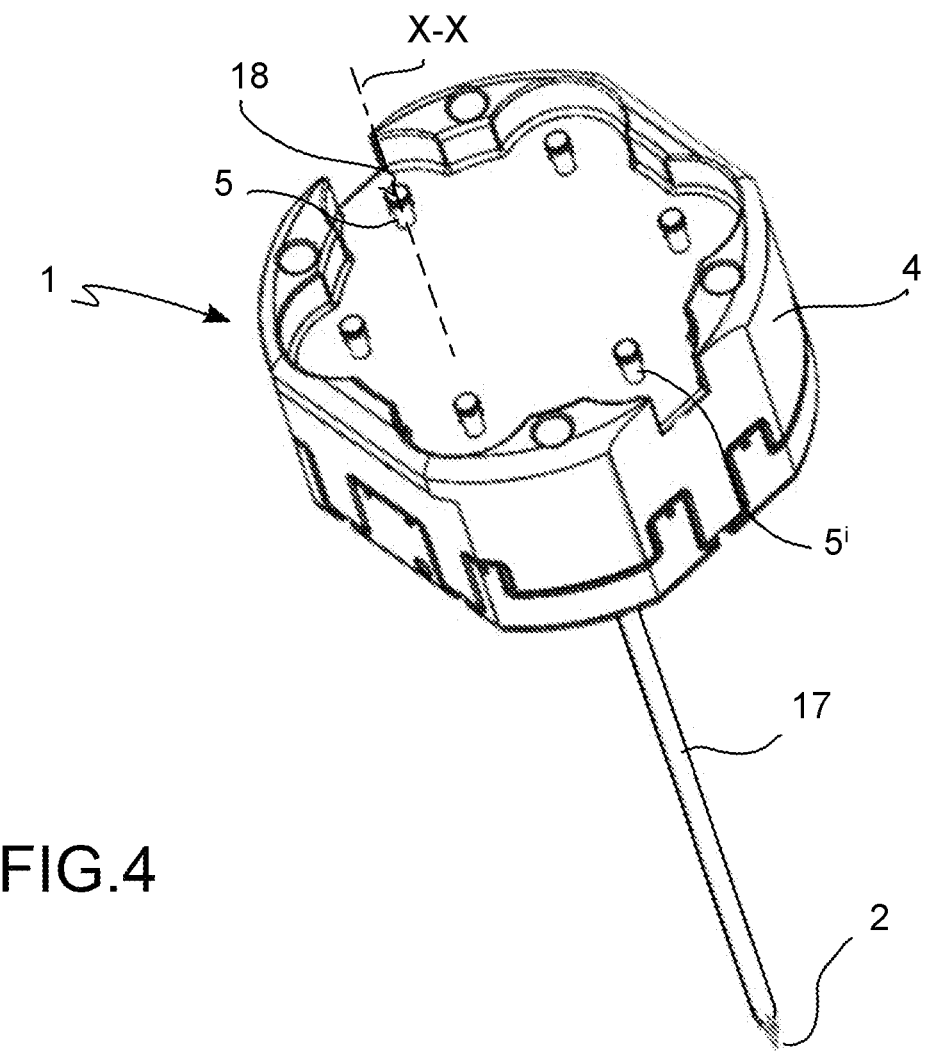
FIG. 4 is an axonometric view showing a surgical instrument, according to an embodiment.

In accordance with an embodiment, as shown for example in FIG. 4, said surgical instrument 1 comprises six elongated transmission bodies 5, each operatively connected to an actuating tendon 3. Preferably said six elongated transmission bodies 5 comprise three pairs of antagonist elongated transmission bodies 5, 5', for actuating three degrees of freedom of the surgical instrument 1 (e.g., pitch, yaw and grip). For example, each pair of tendons ends at a link of the articulating end 2. For example, each pair of tendons can actuate a degree of freedom. In accordance with an embodiment, the surgical instrument 1 comprises six actuating tendons 3, formed by three pairs of antagonist actuating tendons. Preferably, the articulating end 2 comprises links and joints defining the degrees of freedom of at least pitch, yaw and grip of the articulating end 2, and each pair of tendons is connected with a single link of the articulating end 2: for example, a pair of antagonist tendons connected to the same tip link can actuate both the degree of freedom of yaw for that link and the degree of freedom of grip (i.e., opening/closing).

Figure 8:
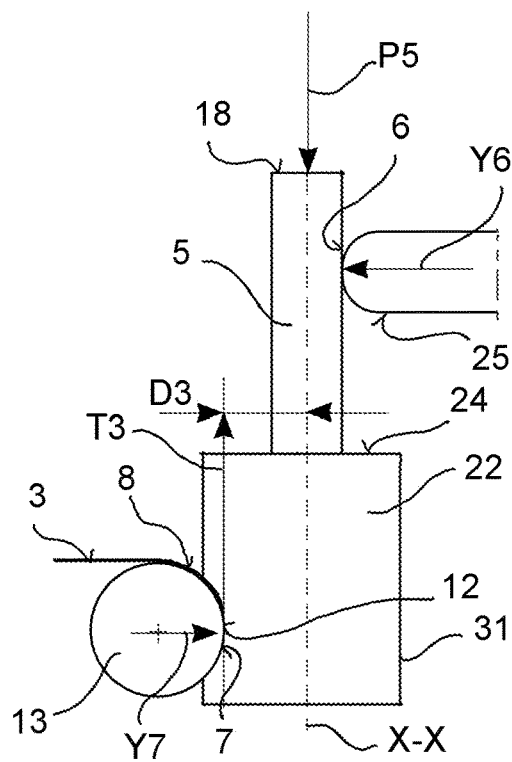
FIG. 8 is a diagram showing the backend portion of FIG. 7, in which the balance of forces is diagrammatically shown.
Figure 9:
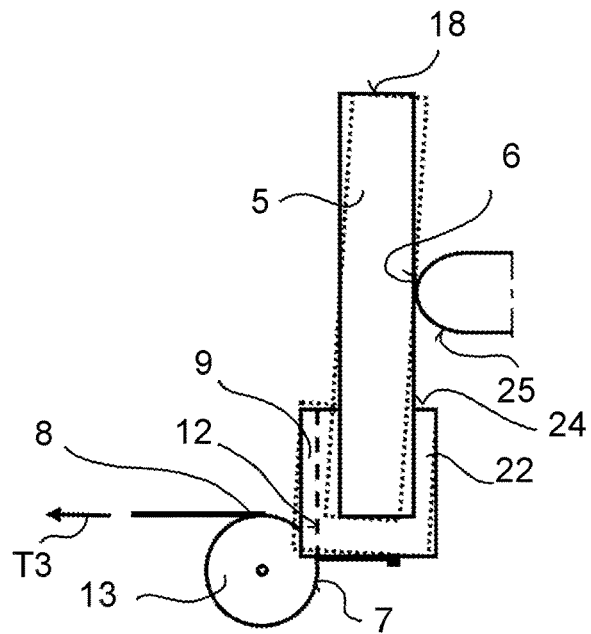
FIG. 9 is a diagram showing a section of a backend portion, according to an embodiment.
Figure 10:
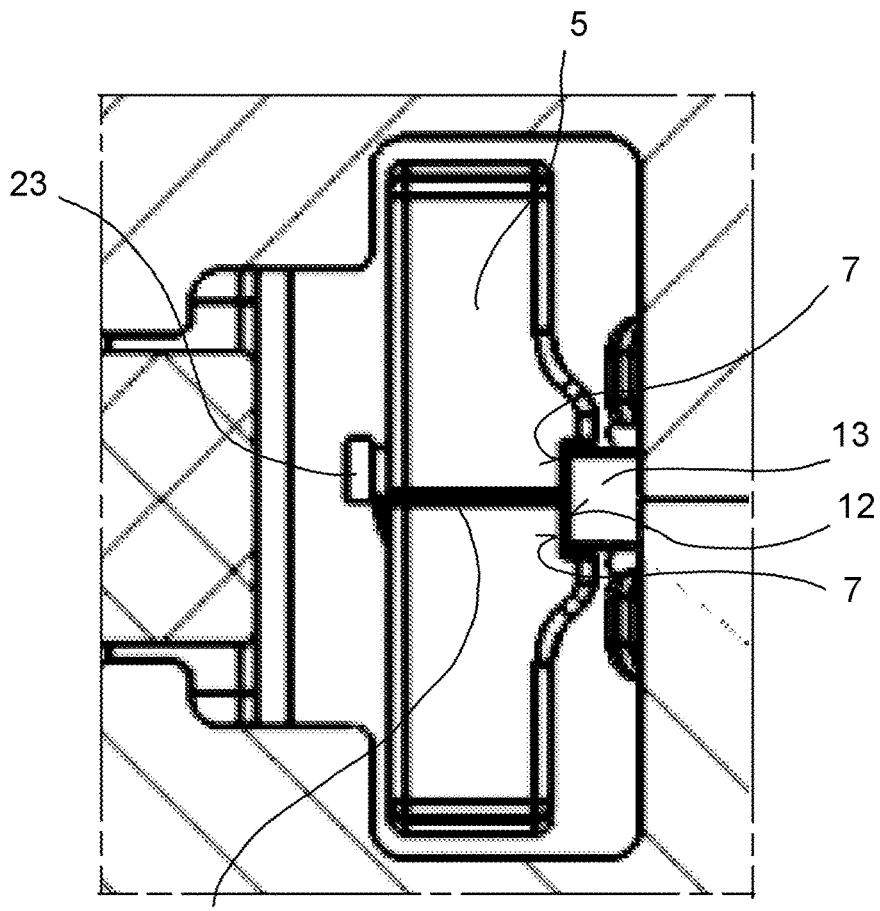
FIG. 10 is a plan view of a backend portion in which a rolling organ received in a rail of an elongated transmission body is visible, according to an embodiment.
Figure 11:
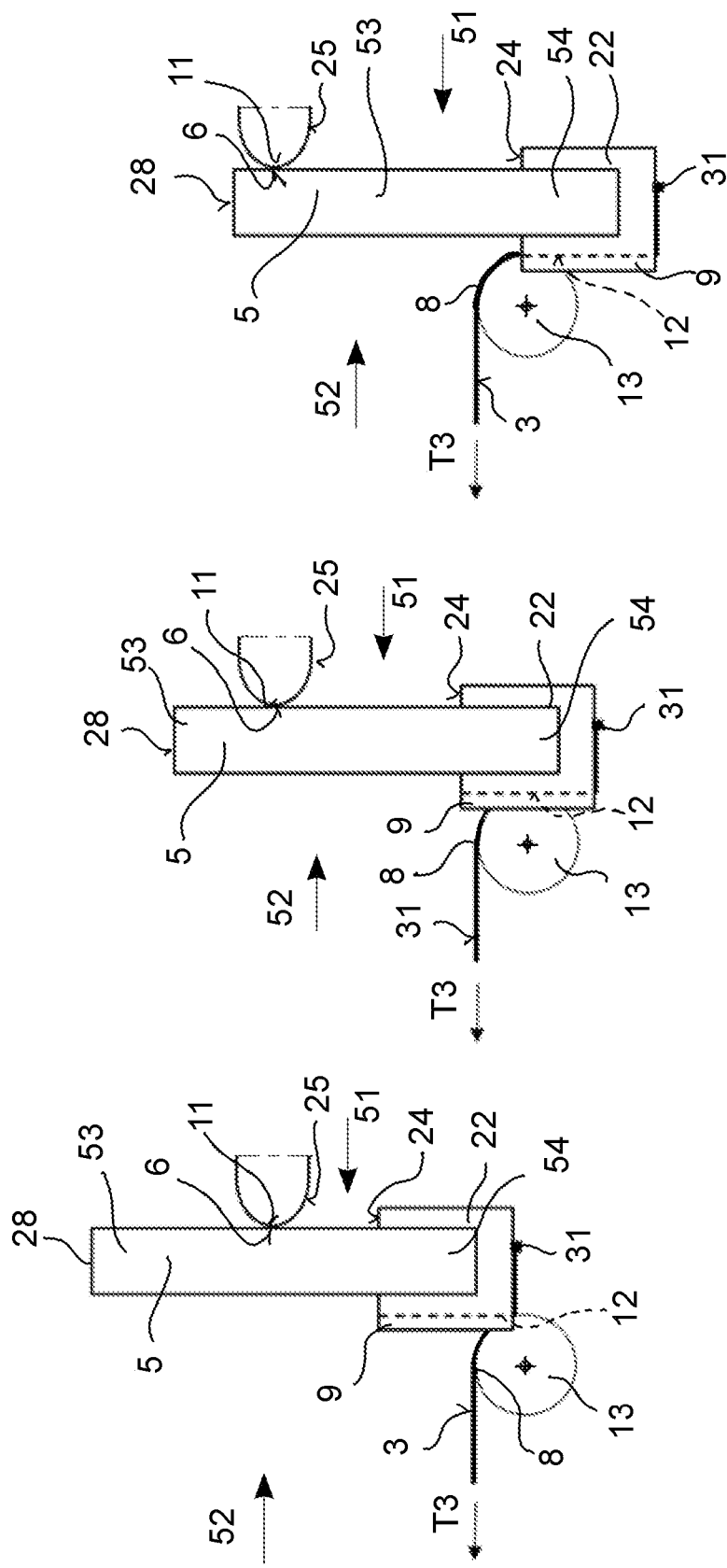
FIGS. 11A, 11B and 11C are diagrams showing a section of a backend portion, according to an embodiment and in various operating configurations.
Figure 12:
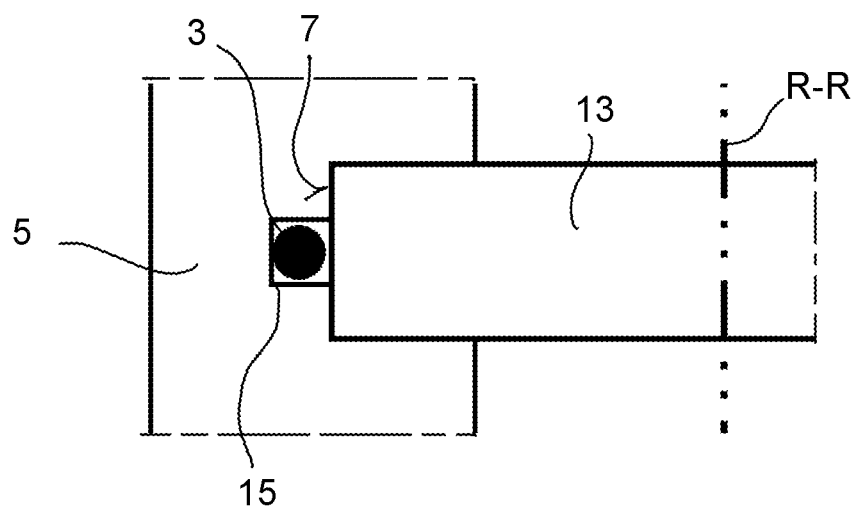
FIG. 12 is a plan view diagram of a backend portion in which a rolling organ received in a rail of an elongated transmission body is visible, in which the rail comprises a recess for receiving the tendon, according to an embodiment.
Figure 13:
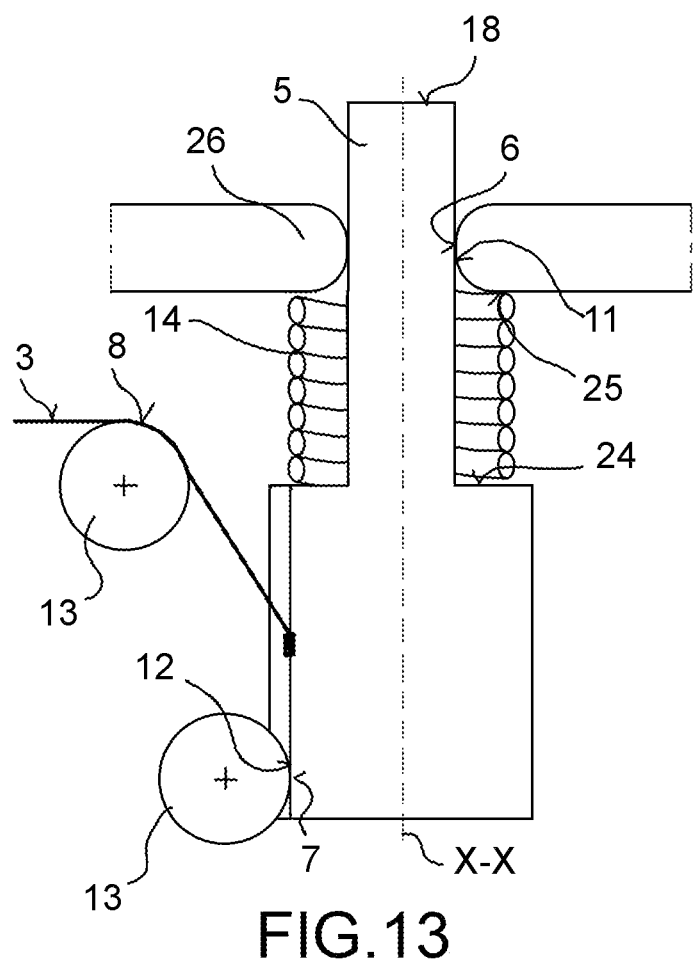
FIG. 13 is a sectional diagram showing a backend portion, according to an embodiment.
Figure 14:
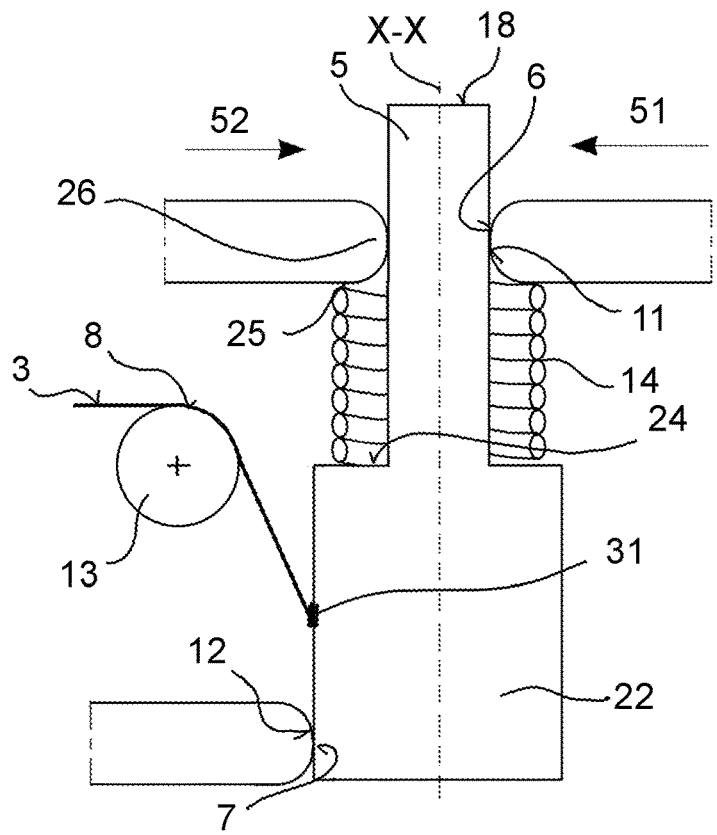
FIG. 14 is a sectional diagram showing a backend portion, according to an embodiment.
Figure 15:
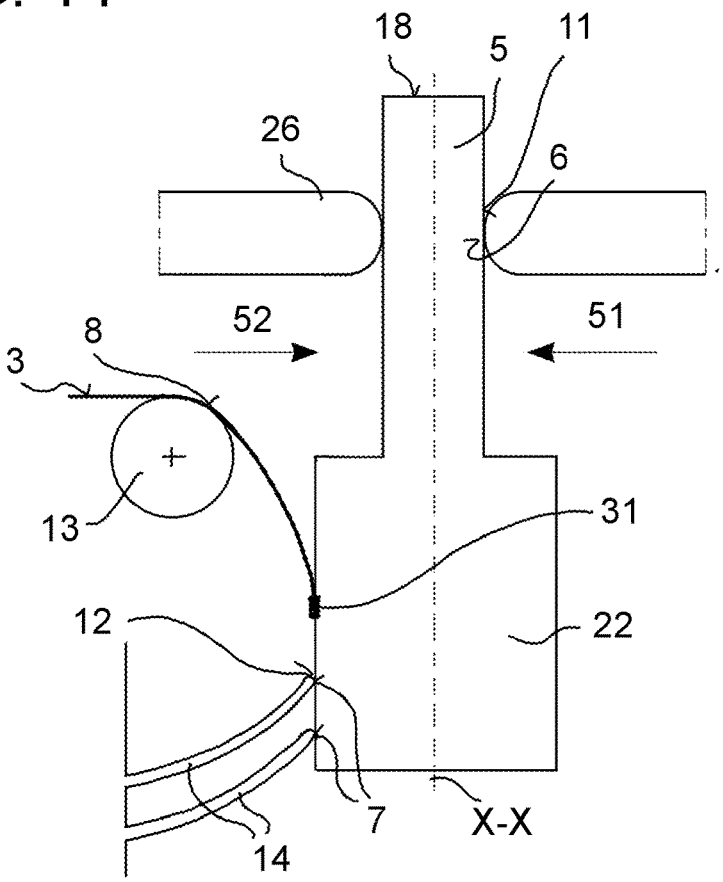
FIG. 15 is a sectional diagram showing a backend portion, according to an embodiment.
Figure 16:
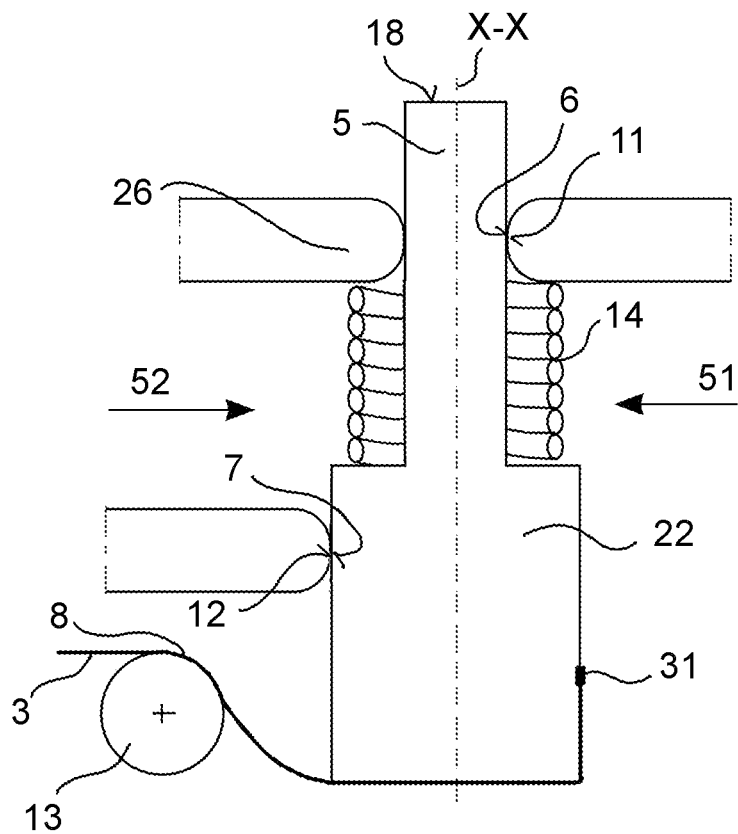
FIG. 16 is a sectional diagram showing a backend portion, according to an embodiment.
Figure 17:
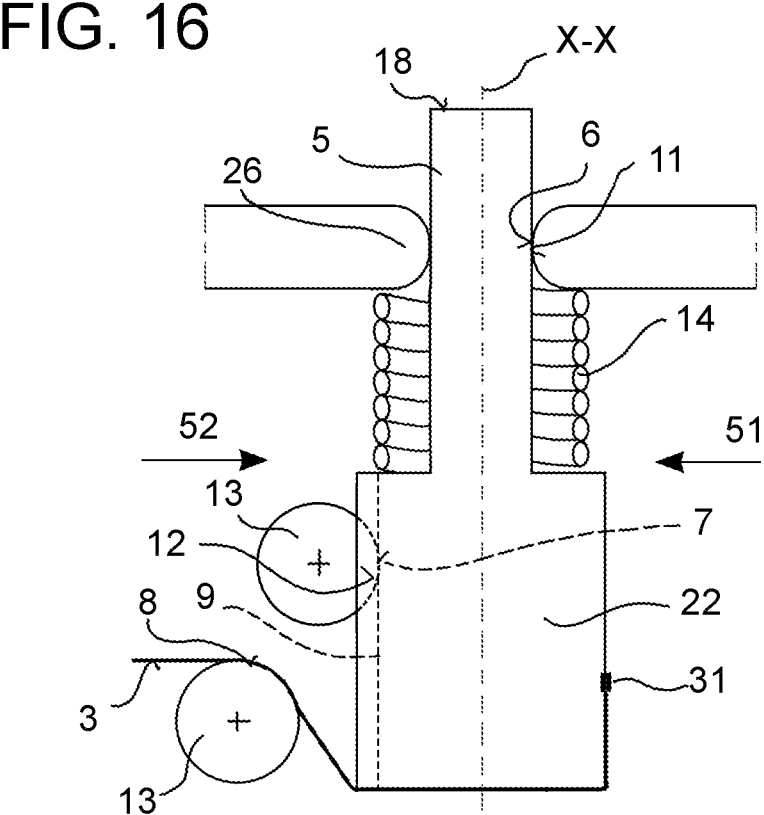
FIG. 17 is a sectional diagram showing a backend portion, according to an embodiment.

With reference to the description above and as show for example in FIGS. 8, 9 and 11 A-C, according to an embodiment, the first resting wall 6 forms a spherical resting element (for example by means of forming an either cylindrical or toroidal convex surface) for the elongated transmission body 5 (for example a cylindrical body such as a rod), and the second resting part 7 and the return element 8 are both formed by said pivotable organ 13, which is dragged in rotation by the axial (longitudinal) motion of the elongated transmission body 5, the at least one actuation tendon 3 is secured to said elongated transmission body 5 and is wrapped around the pivotable organ 13. In this embodiment, the spherical rest (i.e. the sliding contact between said convex first resting wall 6 and said convex second resting part 7) allows to minimize the contact area during sliding and therefore the sliding friction, and at the same time the pivoting organ 13 in rolling contact with the elongated transmission body 5 allows to further reduce the sliding friction, and at the same time the tension of the actuation tendon 3 pulls the elongated transmission body 5 towards the pivoting organ 13. This way, the surface of the contact area with the movable elongated transmission body 5 is minimized, thereby minimizing the resistance to the longitudinal motion of the elongated transmission body 5.

Figure 18:
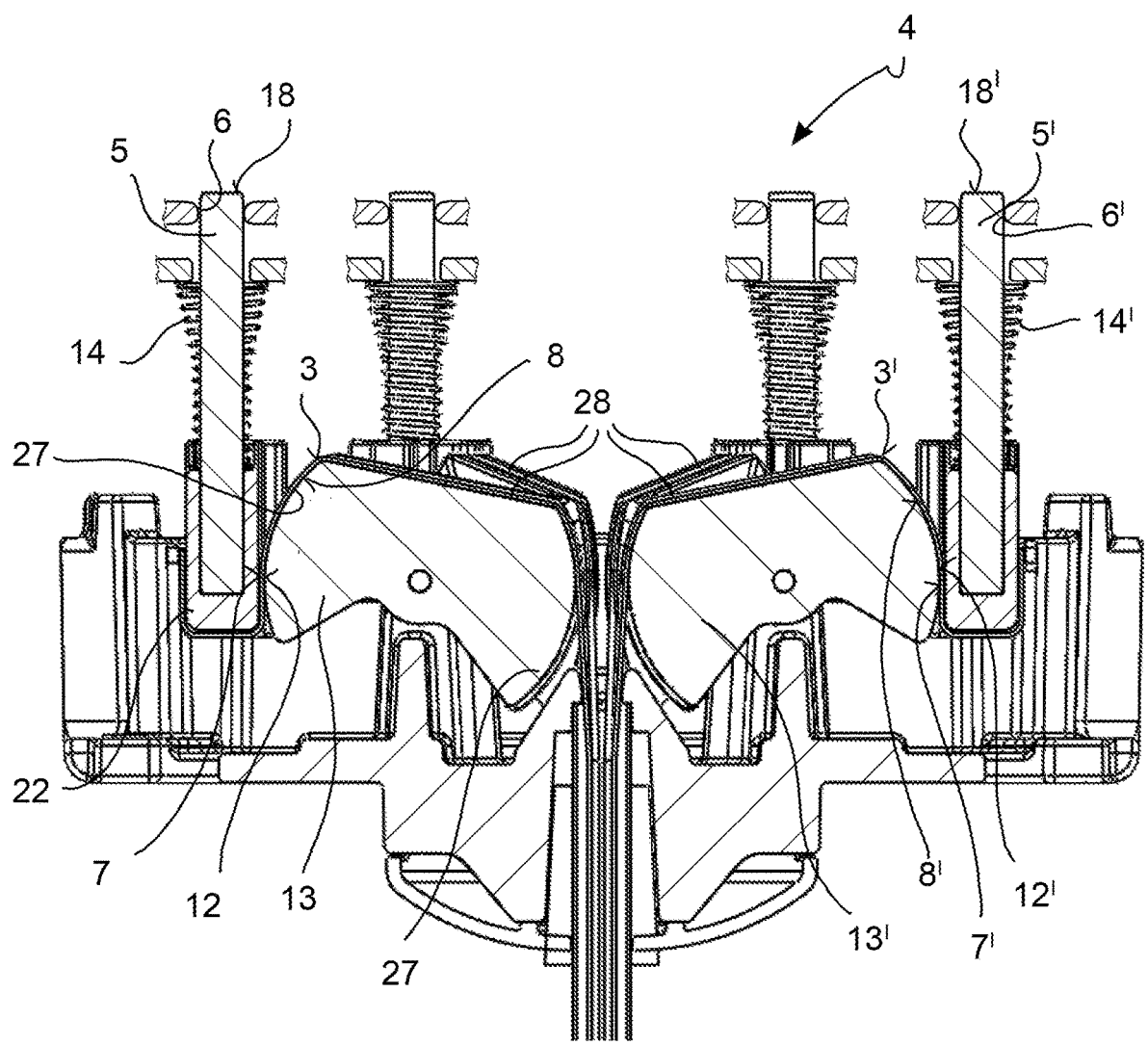
FIGS. 18 and 19 are cross-sectional views showing, respectively elevation and axonometric, a backend portion, according to an embodiment, wherein some parts are transparent for sought of clarity.
Figure 19:
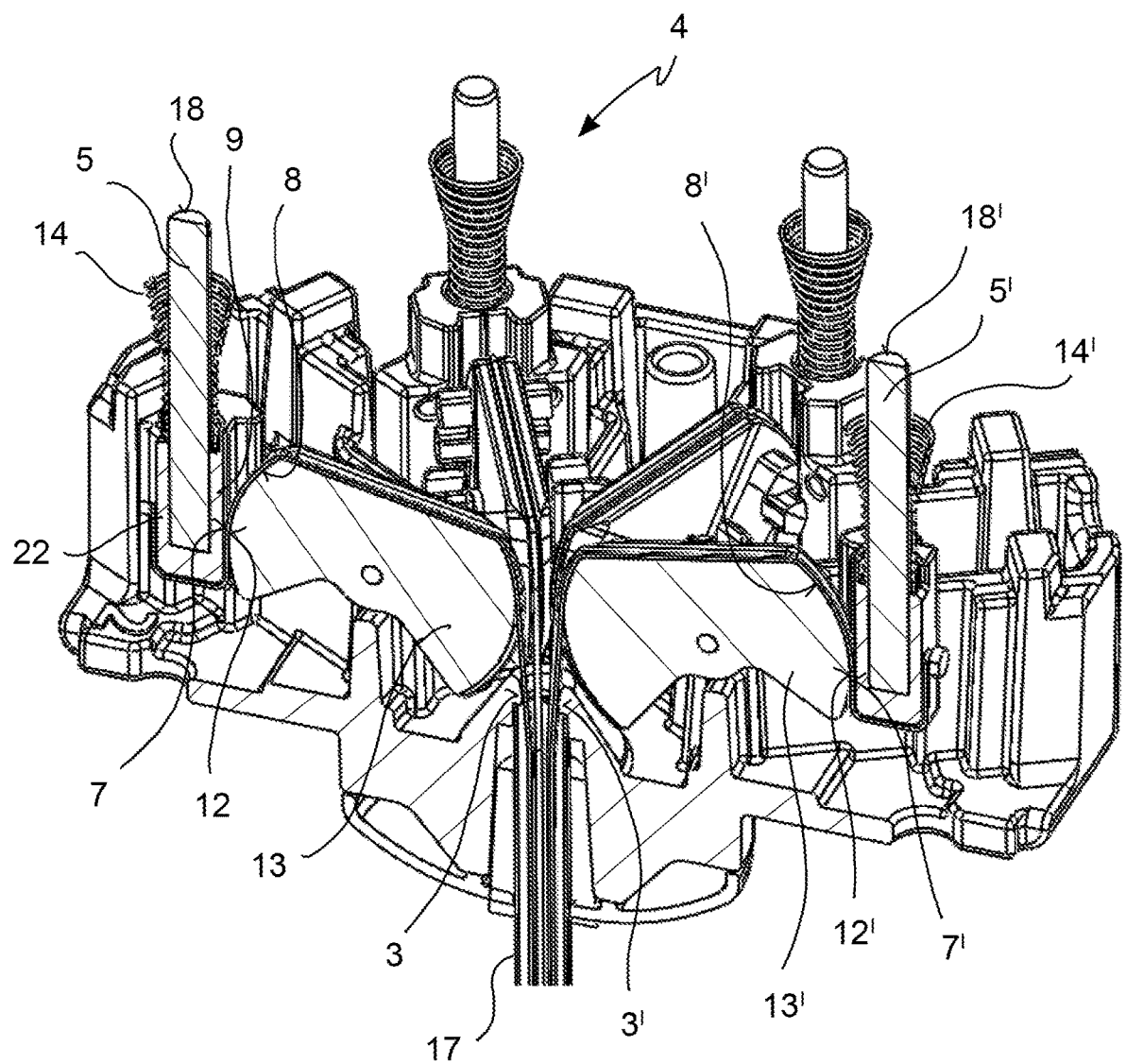

With reference to the description above and as shown, for example, in FIGS. 18 and 19, according to an embodiment, the second resting part 7 and the return element 8 are both formed by said pivoting organ 13 (for example a pulley), which is dragged in rotation by the motion of the elongated transmission body 5, the at least one actuation tendon 3 is secured to the elongated transmission body 5 and is wrapped around said pivoting organ 13. In this embodiment, the pivoting organ 13 may be dimensioned in such a way to reduce to the minimum the angle of rotation of the pivoting organ 13, and for example has diameter substantially equal to the distance between the elongated transmission body 5 and the positioning shaft of the surgical instrument. Thanks to this embodiment, it is possible to shorten the path of the actuation tendon.

The provision of such a pivoting organ 13 with diameter substantially equal to the distance between the elongated transmission body 5 and the positioning shaft of the surgical instrument allows for a simplified assembly line of the components of the backed interface of the surgical instrument as well as of the actuation tendons.

The provision of such a pivoting organ 13 with diameter substantially equal to the distance between the elongated transmission body 5 and the positioning shaft of the surgical instrument also allows for substantially guiding by means of a single body the path of the actuation tendon 3 between the elongated transmission body 5 and the positioning shaft of the surgical instrument. In case a plurality of actuation tendons are provided, that also allows for arranging the tendons of said plurality in rays (i.e. radial pattern) with respect to the hole of the hollow positioning shaft in a precise yet simple way. The radial pattern may allow to manufacture all the actuation tendon of the same length because each tendon path may be made, radially oriented, of the same length. The outer edge of the pivoting organ may comprise a groove to receive the actuation tendon.

The pivoting organ 13 may be dimensioned to reduce its own encumbrance (i.e. size), for example by cutting off a portion of the pivoting organ that does not work when in use (for example by cutting away one or more circular segments), for example cutting off an arc which the actuation tendon 3 does not unwind therefrom when in operative condition. This way, the shape of the pulley (pivoting organ 13) can be optimized.

For example, the pivoting organ 13 may comprise two opposite curved arcs 27 with radius centered in the axis of rotation of the pivoting organ and a straight segment 28 connecting said two opposite arcs 27, wherein the actuation tendon 3 is wrapped around at least a portion of each of said two opposite arcs 27 and it is also adherent (i.e., glued and/or frictional contact) to said straight segment 28.

The provision of a pivotable organ 13 with large diameter as mentioned above, wherein the actuation tendon 3 is wrapped around thereto exerting a tensile load and adherent to at least one segment of the pivotable organ 13, enables the pivotable organ to working substantially as a lever with fulcrum in the rotation axis of the pivotable organ. In other words, such a pivotable organ 13 does not rotate than for a fraction of a turn, back and forth, when in operative conditions. Therefore, it is allowed to adjust the transmission ration between the force applied to elongated transmission element 5 and the tension of the actuation tendon within the shaft 17, by adjusting the position of the fulcrum, that is to say the rotation axis of the pivoting organ 13, as well as the radius of such opposite arcs 27. Therefore, with the term "pivoting organ" it is also intended to mean a lever with fulcrum, for example, coupled to a portion of the case of the backend 4 of the surgical instrument, as well as a pivotable cam.

The elastic element 14 may be a conical axial coil spring.

In accordance with a general embodiment, a robotic surgery system 10 is included, comprising at least one surgical instrument 1 according to any one of the embodiments described above. The robotic surgery system 10 can be suitable for teleoperated robotic surgery according to a master-slave architecture. For example, the robotic surgery system 10 can comprise a master console comprising a master control device which is not grounded and the position and orientation of which is detected by an electromagnetic and/or optical tracking system.

The robotic surgery system 10 comprises at least one robotic manipulator 20 comprising at least one motorized actuator 19 adapted to exert a pushing action P5 on said at least one elongated body 5 of the backend portion 4 of the surgical instrument 1.

Preferably, the surgical instrument 1 is detachably associated with the robotic manipulator 20.

Preferably, the robotic surgery system 10 further comprises at least one electronic control device 21.

Preferably, the robotic surgery system 10 further comprises a sterile barrier, for example a sterile cloth, between the robotic manipulator 20 and the backend portion 4 of the surgical instrument 1.

It is well understood that the combination of features, structures or functions disclosed in one or more of the appended claims forms an integral part of the present description.

By virtue of the features described above, provided either separately or in combination with one another in particular embodiments, it is possible to meet the needs mentioned above, and to obtain the aforementioned advantages, and in particular:

- the inclusion of sliding bushings is avoided;
- with the same longitudinal dimensions, it allows increasing the useful stroke of the elongated body;
- with the same useful stroke of the elongated body, it allows reducing the longitudinal dimensions;
- the traction action of the tendon pulls the elongated body against the rolling organ;
- the elastic element ensures a minimum preload on the tendon;
- the risk of tendon slippage with respect to the return element is minimized;

the elongated body is allowed to oscillate, i.e., tilt with respect to the longitudinal direction, without causing impingements;

a surgical instrument is made which is suitable for an extreme miniaturization of the articulating end and at the same time capable of transmitting actuating forces to the articulating end in a precise, repeatable and safe manner;

the misalignment between the pushing action P5 and the traction action T3 causes the occurrence of a torque which tends to stabilize the system;

a stable, self-stabilizing transmission system is created, which works optimally even with high traction loads on the tendon, and therefore also with high pushing actions;

the volumetric dimensions of the backend portion are kept compact;

the inclusion of said distal section of the elongated body facing the second side, i.e., in sliding rolling rest on said rolling organ, and operatively connected to said actuating tendon, substantially creates a carriage constraint.

It is well understood that the combinations of features disclosed in the appended claims form an integral part of the present disclosure.

In order to meet specific, contingent needs, those skilled in the art can make several changes and adaptations to the above-described embodiments and can replace elements with other functionally equivalent ones, without departing from the scope of the appended claims.

LIST OF NUMERICAL REFERENCES

1. Surgical instrument
2. Articulating end
3. Actuating tendons
4. Transmission interface portion, or backend portion
5. Elongated transmission body
6. Resting wall forming a first resting part
7. Second resting part
8. Return element
9. Longitudinal rail
10. Robotic surgery system
11. First lateral surface
12. Second lateral surface
13. Pivotable organ
14. Elastic element
15. Recess
17. Shaft
18. Interface surface
19. Motorized actuator
20. Robotic manipulator
21. Control device
22. Transversally enlarged portion
23. Further resting wall of the second side
24. Abutment part for the elastic element
25. Abutment part for the elastic element
26. Further wall of the hole edge
27. Arc of the pivotable organ
28. Straight segment of the pivoting organ
31. Tendon head
51. First transversal side of the elongated body
52. Second transversal side of the elongated body
53. First longitudinal section of the elongated body
54. Second longitudinal section of the elongated body
X-X. Longitudinal direction
D3. Distance
P5. Pushing action
T3. Traction action
Y6, Y7. Transversal reaction

The invention claimed is:

1. A surgical instrument for robotic surgery comprising:
a tendon-actuated articulating end,
at least one actuating tendon, and
a backend portion comprising:
at least one elongated transmission body moveable along a longitudinal direction, which coincides with or is parallel to a longitudinal extension axis of said at least one elongated transmission body;
at least a first resting wall, forming a first resting part for a first transversal side of the at least one elongated transmission body;
at least a second resting part for a second transversal side, opposite to said first transversal side, of the at least one elongated transmission body;
at least one return element for the at least one actuating tendon;
wherein:
said at least one actuating tendon is operatively connected to said elongated transmission body and is operatively connected to said at least one return element;
the at least one elongated transmission body comprises on the first transversal side thereof a first lateral surface, which slidably rests against said at least a first resting wall;
said at least a first resting wall comprises a convex resting surface; and
wherein:
the at least one elongated transmission body comprises on the second transversal side thereof a second lateral surface, which slidably rests against said second resting part;
said backend portion further comprises at least one pivotable organ and said second resting part belongs to said pivotable organ, wherein the sliding rest of the second lateral surface of the elongated transmission body on the second resting part determines rolling of the pivotable organ; and
wherein:
said at least one actuating tendon is integral with said elongated transmission body;
said at least one return element locates traction action applied by the actuating tendon apart from the longitudinal axis of the elongated transmission body, so that said actuating tendon applies the traction action generating a torque to bring the second transversal side of the at least one elongated transmission body towards said second resting part of the pivotable organ and to bring the first transversal side of the elongated transmission body towards the convex resting surface of the first resting part.

2. The surgical instrument according to claim 1, wherein said pivotable organ comprises said return element.

3. The surgical instrument according to claim 2, wherein said at least one elongated transmission body comprises a longitudinal rail receiving at least one portion of said pivotable organ.

4. The surgical instrument according to claim 3, wherein between the second transversal side of the at least one elongated transmission body and the at least one pivotable organ a recess is included for receiving the actuating tendon, thereby avoiding interposing with contact the actuating tendon between the pivotable organ and the elongated transmission body.

5. The surgical instrument according to claim 4, wherein an axis of rotation of the at least one pivotable organ is fixed with respect to said backend portion of the surgical instrument, and said axis of rotation is fixed with respect to said first resting wall of said backend portion;

and/or wherein said axis of rotation is oriented transversally with respect to the longitudinal direction.

6. The surgical instrument according to claim 1, wherein said backend portion further comprises at least one elastic element operatively connected to said at least one elongated transmission body which biases said at least one actuating tendon.

7. The surgical instrument according to claim 6, wherein the first lateral surface of the first transversal side of the elongated transmission body is substantially cylindrical.

8. The surgical instrument according to claim 1, wherein the resting surface of the first resting wall forms a spherical sliding contact for said first transversal side of the at least one elongated transmission body.

9. The surgical instrument according to claim 1, comprising a plurality of actuation tendons arranged in rays with respect to a central portion of the backed portion.

10. The surgical instrument according to claim 1, wherein said pivoting organ has extension, substantially equal to a distance between the elongated transmission body and the shaft of the surgical instrument; and wherein preferably, the actuation tendon is adherent to at least a segment of the pivotable organ.

11. The surgical instrument according to claim 1, wherein said at least one actuating tendon comprises a head that is terminally secured to said elongated transmission body.

12. The surgical instrument according to claim 1, wherein said convex resting surface of the first resting wall is substantially cylindrical.

13. The surgical instrument according to claim 1, wherein the first lateral surface of the first transversal side of the elongated transmission body is curved and convex.

14. The robotic surgery system comprising:
at least one surgical instrument according to claim 1, and
at least one robotic manipulator comprising at least one motorized actuator adapted to exert a pushing action on said at least one elongated transmission body of the backend portion of the surgical instrument.

* * * * *